United States Patent
Oslie et al.

(10) Patent No.: US 12,262,110 B2
(45) Date of Patent: Mar. 25, 2025

(54) MEDICAL IMAGING SCOPE WITH CAPACITIVE SENSOR UNITS

(71) Applicant: KARL STORZ Imaging, Inc., Goleta, CA (US)

(72) Inventors: Larry Oslie, Santa Barbara, CA (US); Jonathan Bormet, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 245 days.

(21) Appl. No.: 18/060,156

(22) Filed: Nov. 30, 2022

(65) Prior Publication Data
US 2024/0179394 A1   May 30, 2024

(51) Int. Cl.
| | |
|---|---|
| *A61B 1/00* | (2006.01) |
| *A61B 1/045* | (2006.01) |
| *G06F 3/044* | (2006.01) |
| *H04N 23/50* | (2023.01) |
| *H04N 23/56* | (2023.01) |
| *H04N 23/62* | (2023.01) |
| *H04N 23/74* | (2023.01) |

(52) U.S. Cl.
CPC ........... *H04N 23/62* (2023.01); *A61B 1/0004* (2022.02); *A61B 1/045* (2013.01); *G06F 3/044* (2013.01); *H04N 23/555* (2023.01); *H04N 23/56* (2023.01); *H04N 23/74* (2023.01)

(58) Field of Classification Search
None
See application file for complete search history.

(56) References Cited

U.S. PATENT DOCUMENTS

| | | | |
|---|---|---|---|
| 2019/0000302 A1* | 1/2019 | Doser | A61B 1/00066 |
| 2021/0344830 A1* | 11/2021 | Shan | H04N 23/64 |
| 2022/0087748 A1* | 3/2022 | Savall | A61B 34/25 |
| 2023/0181266 A1* | 6/2023 | Hallen | G16H 40/63 606/1 |
| 2023/0371791 A1* | 11/2023 | Fancher | A61B 1/00066 |
| 2023/0381398 A1* | 11/2023 | Lynn | A61B 17/3205 |
| 2023/0408074 A1* | 12/2023 | Parajuli | F21V 23/0485 |
| 2024/0122579 A1* | 4/2024 | Dhatt | A61B 8/58 |

* cited by examiner

*Primary Examiner* — Frank Johnson
(74) *Attorney, Agent, or Firm* — David N. Villalpando; Jacqueline Cohen (57) ABSTRACT

Provided is a camera head having a capacitive sensing unit disposed along the outer surface of the camera head. The capacitive sensing unit includes a plurality of capacitive sensors. The camera head includes an electronic controller operable to process an actuation of the plurality of capacitive sensors to control a camera control function and determine a medical procedure and/or the identity of the user.

15 Claims, 7 Drawing Sheets

MEDICAL IMAGING SCOPE WITH CAPACITIVE SENSOR UNITS

TECHNICAL FIELD

The disclosure generally relates to medical imaging scopes and, more specifically, to a camera head configured to facilitate use by processing a grip.

BACKGROUND

Figure 1:
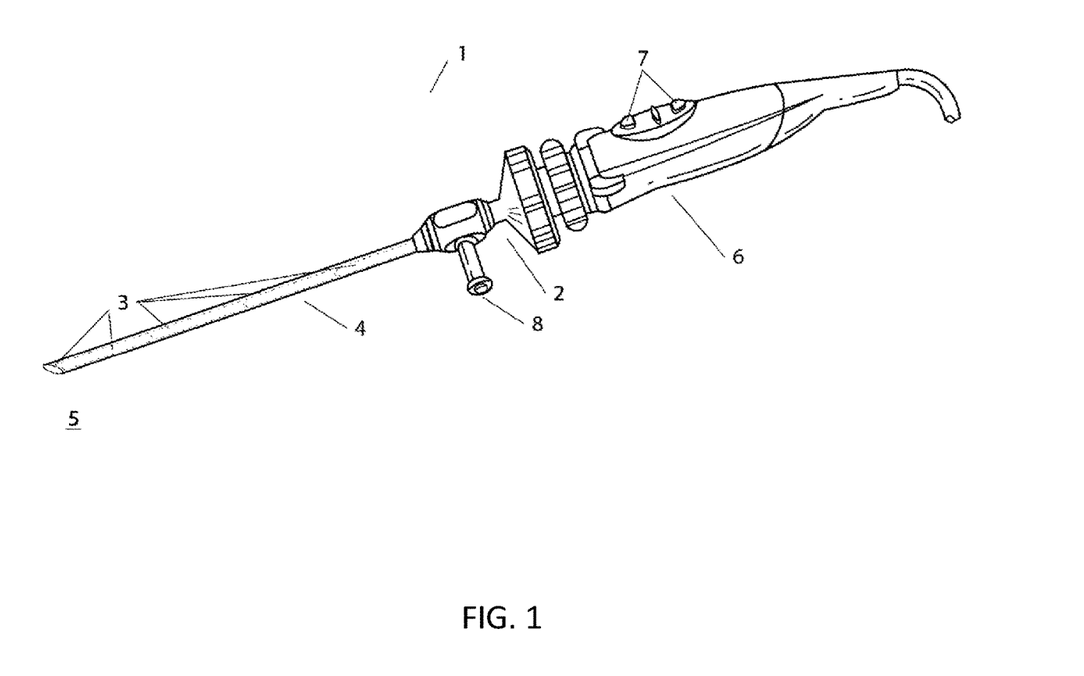
FIG. 1 is a diagram of a prior art endoscopic system.

A typical prior art optical endoscopic system 1, as illustrated in FIG. 1, usually includes a first imaging lens (e.g., an objective) or lenses followed by a series of carrier lenses (e.g., relays), collectively an optical assembly 3 in the endoscope 4, which capture and transmit an optical image from inside of an enclosed area 5, such as an internal region of a human or animal body, to the outside of the enclosed area, where the image light can be captured and/or analyzed. The proximal end of the endoscope 2 may be attached, via direct coupling or an adaptor, to a camera head 6 or an eye-piece for viewing. The camera head 6 usually includes an optical system comprising lenses for receiving the optical image and forming a real optical image onto one or more image sensors contained therein. The digital image or images captured by the image sensor(s) can then be transmitted to a camera control unit or other similar modules for analysis, processing, and/or display.

The endoscopic system 1, and in particular the camera head 6, is typically preprogrammed, wherein some of the buttons 7 may be assigned a camera control function, and some buttons are configured to control the selected camera control function. Thus, the user must either reprogram the buttons to achieve a desired configuration or operate the endoscopic system in the manner in which the buttons are preprogrammed. Accordingly, it remains desirable to have an endoscopic system wherein the use of the camera control functions are intuitive or programmed to a user preference.

SUMMARY

A camera head communicatively coupled to a camera control unit is provided. The camera control unit is configured to process data from the camera head to generate an image. The camera head includes a first capacitive sensing unit and an electronic controller. The first capacitive sensing unit is disposed along at least one surface of the camera head and is configured to detect a grip. The electronic controller is communicatively coupled to the first capacitive sensing unit and operable to process the grip to determine a profile of the grip. A memory storage unit is configured to store a plurality of grip profiles, each of the plurality of grip profiles being associated with a predetermined configuration of the one or more camera control functions. The electronic controller processes the profile of the grip to adjust the camera head to the predetermined configuration for operating the one or more camera control functions associated with the detected profile.

In one aspect, the profile is processed to determine a handedness of the user, wherein the electronic controller may further process the handedness of the user to adjust the one or more camera control functions to the predetermined configuration.

In another aspect, the electronic controller processes the profile of the grip to determine an identification of a user and adjusts the camera head to the predetermined configuration associated with the identified user. In such an aspect, the electronic controller is configured to turn off at least one of the one or more camera control functions when the grip is not detected. For instance, the camera control function may be a light source.

In yet another aspect, the camera head further includes an input unit disposed on the surface of the camera head, wherein the input unit is configured to select and control the one or more camera control functions. The one or more camera control functions may be a zoom, a focus, an orientation, and a brightness of an image. The input unit may be a trackpad, a second capacitive sensing unit having a plurality of second capacitive sensors, a second capacitive sensing unit, and a plurality of buttons, each of the plurality of buttons configured to select one of the plurality of camera control functions, wherein the second capacitive sensing unit is configured to control the selected one of the plurality of camera functions. The second capacitive sensing unit may be bound by the first capacitive sensing unit. The second capacitive sensing unit is configured to detect a sliding motion. In aspects where the input unit includes buttons, each of the buttons in the plurality of buttons may be configured to illuminate when the selected one of the plurality of camera control functions is actuated.

The second capacitive sensing unit includes a plurality of second capacitive sensors, wherein the electronic controller is programmed to process the profile to determine a handedness and generate a configuration for control, the configuration for control being an arrangement of second capacitive sensors of the plurality of second capacitive sensors to generate a corresponding one of the plurality of camera control functions. In such an aspect, the configuration for control includes a first configuration and a second configuration symmetrical to the first configuration. The configuration for control may include at least one capacitive sensor from the plurality of second capacitive sensors, and the electronic controller is programmed to process an actuation of the at least one capacitive sensor to select a camera control function from the plurality of camera control functions and at least two capacitive sensors from the plurality of second capacitive sensors are configured to control the selected camera control function. The camera head may further include function light disposed on the camera head, wherein the electronic controller is configured to process the selected camera control function and illuminate the function light to display a light corresponding to the selected camera control function.

An endoscopic imaging system is also provided. The endoscopic imaging system includes a camera head having a first capacitive sensing unit, an electronic controller, and a memory storage unit. The first capacitive sensing unit is disposed along a surface of the camera head. The first capacitive sensing unit is configured to detect a grip. The electronic controller is communicatively coupled to the first capacitive sensing unit and operable to process the grip to determine a profile of the grip. The memory storage unit is configured to store a plurality of grip profiles, each of the plurality of grip profiles being associated with a predetermined configuration of the one or more camera control functions. An endoscope is attached to the camera head. A camera control unit includes a system controller and a system memory. The camera control unit is communicatively coupled to the camera head. The electronic controller processes the profile of the grip to adjust the camera head to the predetermined configuration for operating the one or more camera control functions associated with the detected profile.

In one aspect, the profile may be processed to determine a handedness of the user. The electronic controller may further process the handedness of the user to adjust the one or more camera control functions to the predetermined configuration, wherein the system controller processes the predetermined configuration to generate an image according to the predetermined configuration.

In yet another aspect, the electronic controller processes the profile of the grip to determine an identification of a user and adjusts the camera head to a preference associated with the identified user. In such an aspect, the preference is a setting of the at least one or more camera control functions, wherein the system controller processes the preference to generate an image according to the preference.

In one aspect, the electronic controller instructs the system controller to turn off at least one of the one or more camera control functions when the grip is not detected.

In another aspect, the endoscope includes a light-emitting element configured to provide light, and the camera control function is the light.

In yet another aspect, the medical imaging scope further includes an input unit disposed on the camera head. The input unit is configured to select and control the one or more camera control functions. The camera control functions may be a zoom, a focus, an orientation, and a brightness of an image.

The input unit may be a trackpad, a second capacitive sensing unit, and a second capacitive sensing unit, including a plurality of buttons. In such an aspect, the input unit is bound by the first capacitive sensing unit. In instances where the input unit includes buttons, each button is configured to select one of the plurality of camera control functions, wherein the second capacitive sensing unit is configured to control the selected one of the plurality of camera control functions. For instance, the second capacitive sensing unit is configured to detect a sliding motion of a finger, and the electronic controller processes the sliding motion to control the selected camera control function. Each of the buttons in the plurality of buttons may be configured to illuminate when the selected camera control function is actuated.

In one aspect where the second capacitive sensing unit includes a plurality of second capacitive sensors, the electronic controller is programmed to process the profile to determine a handedness and generate a configuration for control. The configuration for control is an arrangement of second capacitive sensors of the plurality of second capacitive sensors to generate a corresponding one of the plurality of camera control functions. For example, the configuration for control includes a first configuration and a second configuration symmetrical to the first configuration. In such an aspect, the configuration for control includes at least one capacitive sensor from the plurality of second capacitive sensors. The electronic controller is programmed to process an actuation of the at least one capacitive sensor to select a camera control function and is configured to process an actuation of at least two capacitive sensors to control the selected camera control function.

In yet another aspect, the endoscopic imaging system includes a function light disposed on the camera head, wherein the electronic controller is configured to process the selected camera control function and illuminate the function light to display a light corresponding to the selected camera control function.

A method of operating an imaging system is also provided. The method includes the steps of providing a camera head having a first capacitive sensing unit disposed along at least one surface of the camera head, the camera head including a memory storage unit configured to store a plurality of grip profiles, each of the plurality of grip profiles being associated a predetermined configuration of the one or more camera control functions. The camera head further includes an electronic controller operable to process a grip to determine a profile of the grip; and determine, by the electronic controller, the predetermined configuration for operating the one or more camera control functions associated with the detected profile.

The method may further include the step of determining, by the electronic controller, a handedness of the user. In such an aspect, the handedness of the user is determined by a predetermined pattern of a response from the plurality of first capacitive sensors.

The method may further include the step of determining, by the electronic controller, the identity of the user.

The method may further include the step of providing an input unit disposed on the camera head. The input unit is configured to select and control one of a plurality of camera control functions. In one aspect, the input unit is a trackpad or a second capacitive sensing unit. In one aspect, the second capacitive sensing unit includes a plurality of buttons. In one aspect, the second capacitive sensing unit includes a plurality of second capacitive sensors, and the second capacitive sensing unit is bound by the first capacitive sensing unit.

The method, wherein the input further includes a plurality of buttons, each of the plurality of buttons configured to select one of the plurality of camera control functions, wherein the second capacitive sensing unit is configured to control the selected one of the plurality of camera control functions. In one aspect, the second capacitive sensing unit is configured to detect a sliding motion.

The method may further include the step of processing the detected handedness or identity of the user to generate a configuration for control, the configuration for control being an arrangement of second capacitive sensors of the plurality of second capacitive sensors to generate a corresponding one of the plurality of camera control functions. In such an aspect, the configuration for control includes a first configuration and a second configuration symmetrical to the first configuration. The configuration for control includes at least one capacitive sensor from the plurality of second capacitive sensors, and the electronic controller is programmed to process an actuation of the at least one capacitive sensor to select a camera control function and processes an actuation of at least two capacitive sensors to control the selected camera control function.

BRIEF DESCRIPTION OF THE DRAWINGS

The present disclosure will become more fully understood from the detailed description given herein, and the accompanying drawings, which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refer to the first elements' position along a common optical path that includes first and other elements. For example, a lens group optically arranged between an image sensor and an objective means that the lens group occupies a portion of the optical path that light travels (e.g., from the objective to the image sensor) for capturing images or video.

Because digital cameras and fluorescence imaging sensors (referenced herein as "FI sensors") and related circuitry for signal capture and processing are well-known, the present description will be directed in particular to elements forming part of, or cooperating more directly with, a method and apparatus in accordance with the disclosure. Elements not specifically shown or described herein are selected from those known in the art. Moreover, certain aspects of the embodiments to be described are provided in software. Given the system as shown and described according to the disclosure in the following materials, software not specifically shown, described, or suggested herein that is useful for implementation of the disclosure is conventional and within the ordinary skill in such arts.

An imaging system includes a camera head and an endoscope. The endoscope may be removably attached to the camera head. A capacitive sensing unit is disposed along an outer surface of the camera head. The capacitive sensing unit includes a plurality of capacitive sensors (or sensor elements), which may be arranged along the surface of the camera head. The camera head includes an electronic controller operable to process an actuation of the plurality of capacitive sensors to control a camera control function, controlling the rotation the image displayed, adjusting the intensity of an illumination source, or adjusting focus, optical or digital zoom, or image contrast. As used herein, a camera control function refers to a function which changes an attribute within the imaging system and/or manipulates an image generated by the camera head or a camera control unit, including functions such as rotating the displayed image, optical or digital zooming, focusing, adjusting the intensity of the illumination source, turning on an illumination source, and the like. In other embodiments, the actuation of the capacitive sensing unit is processed to determine a handedness of the user or an identification of the user. The disclosure may be applicable to more than one type of device enabled for image capture, such as endoscopes, digital microscopes, and other medical imaging devices.

Figure 2:
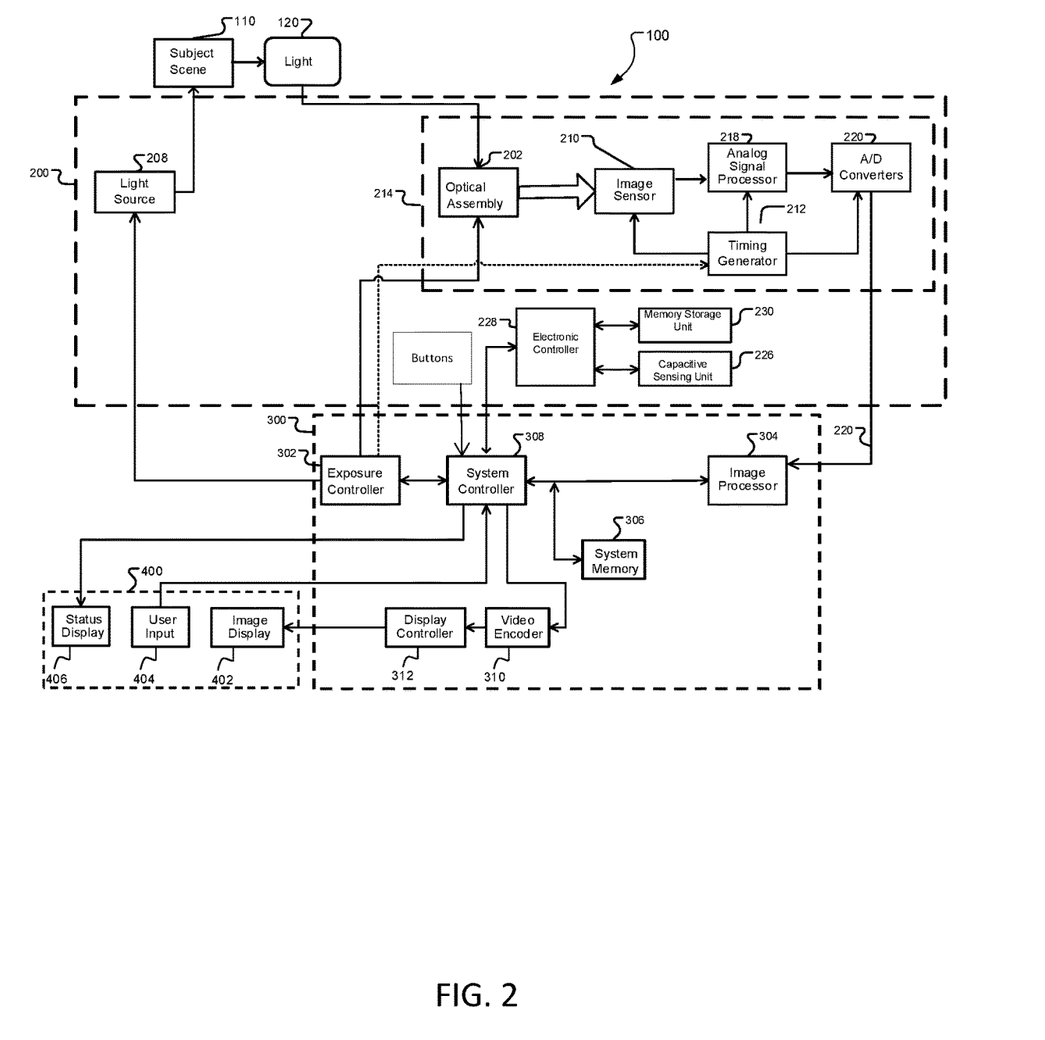
FIG. 2 is a hardware block diagram of an example endoscopic system, including a medical imaging scope, a camera control unit, and a user interface.

Referring to FIG. 2, shown is a system hardware block diagram of an exemplary embodiment of an imaging system 100. Imaging system 100 includes a medical imaging scope 200, a camera control unit (referred to herein as "CCU") 300, and a user interface 400 (e.g., graphical user interface (GUI), system controllers, etc.), having one or more image displays 402. The medical imaging scope 200 of the imaging system 100 is a standard visible light medical imaging scope 200. However, this is not limiting, and features and techniques herein may be employed with many types of endoscopes and borescopes-including visible light/fluorescence imaging (FI) scopes and video endoscopes. Of the depicted blocks, medical imaging scope 200 includes an endoscope 206 and a camera head 204 (see FIGS. 3-6B). The medical imaging scope includes at least one optical assembly 202, and each of the endoscope 206 and the camera head 204 may house one or more elements of the optical assemblies 202 to collect, relay, and/or condition light 120 from the subject scene 110. Endoscope 206 is coupled to camera head 204 and includes an image sensor 210 fixedly mounted within camera head 204.

Medical imaging scope 200 further includes a light source (illumination source) 208 for illuminating a subject scene 110. The light source 208 may be configured to illuminate a subject scene 110, and for FI imaging also provide fluorescence excitation illumination. Light source 208 may include light-emitting elements configured to provide light throughout a desired spectrum, including one or more visible light-emitting elements and/or one or more fluorescent excitation light-emitting elements. Furthermore, light source 208 may include fiber optics passing through the medical imaging scope 200, which may be elements of the light source 208 or may be coupled thereto, or other light-emitting arrangements, such as LEDs or laser diodes positioned at or emanating from or near the proximal end of the medical imaging scope 200.

As shown in FIG. 2, light 120 reflected, scattered, or emitted from the subject scene 110 is collected by elements of the optical assembly 202 and relayed and focused toward image sensor 210 by other elements of the optical assembly.

Figure 3:
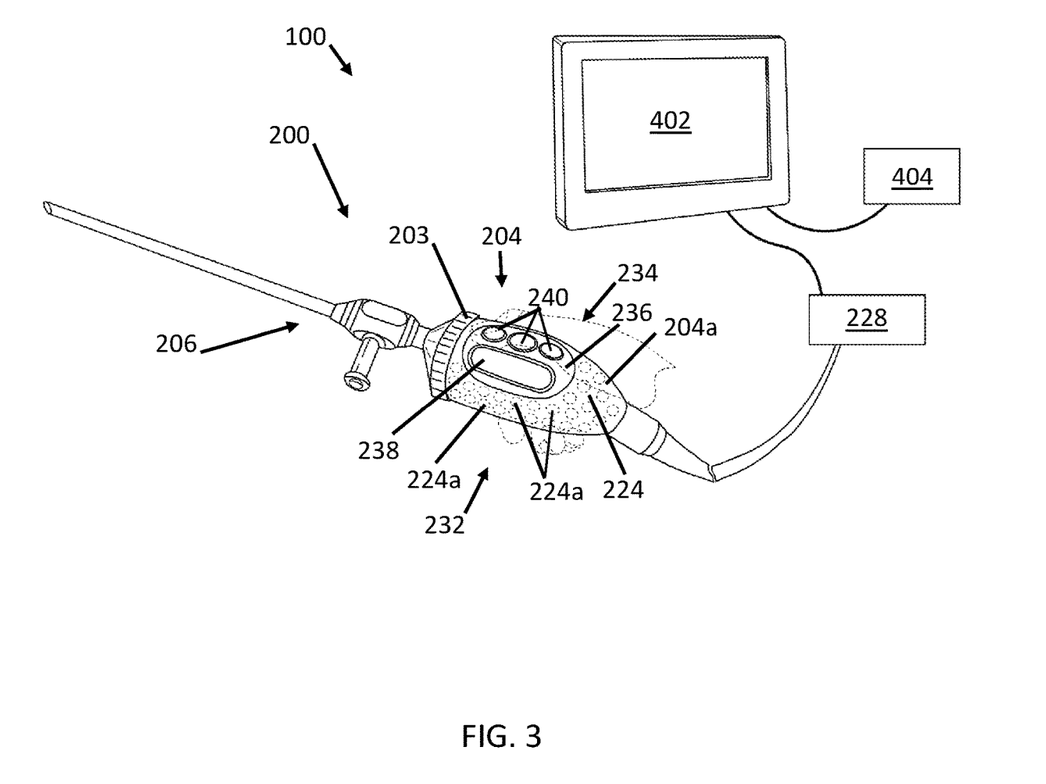
FIG. 3 is an illustrative depiction of a medical imaging scope held in the right hand of a user in accordance with the principles of an embodiment described herein.

Optical assembly 202 includes at least one lens (not shown), which may be a wide-angle lens such that optical assembly 202 captures light representing a wide field of view of the subject scene 110. Portions of the optical assembly 202 may be disposed in camera head 204 (FIG. 3A), while other portions may be disposed in endoscope 206 (FIG. 3A). In some embodiments, the camera head 204 contains additional control electronics. The image sensor 210 is located in the camera head 204. In such an aspect, various endoscopes 206 (FIG. 3A) may be attached to the camera head 204 (FIG. 3A), and light collected from the subject scene 110 is captured by the image sensor 210 in the camera head 204.

Elements of the optical assembly 202 may be contained within a single imaging device with the image sensor 210. In an embodiment, image sensor 210 may include separate red (R), green (G), and blue (B) sensor arrays or a single R, G, or B array with color-sensitive individual pixels. Image sensor 210 converts the incident light to an electrical signal by integrating charge for each picture element (i.e., pixel).

The solid-state image sensor 210 may be an active pixel complementary metal oxide semiconductor sensor (CMOS APS), a charge-coupled device (CCD), or other suitable image sensors known in the art to convert visible and/or infrared light into electrical signals. It should also be noted that image sensor 210 may comprise several individual image sensors.

Timing generator 212 produces various clocking signals to select rows and pixels and is configured to synchronize the operation of image sensor 210. The image sensor unit 214 may include the solid-state image sensor 210, analog signal processor 218, analog/digital (A/D) converter 220, and timing generator 212. The individual components of the image sensor unit 214 can be fabricated as a single integrated circuit (as is commonly done with CMOS image sensors), or they can be separately fabricated integrated circuits.

The total amount of light 120 reaching the image sensor(s) 210 is regulated by the intensity of the light source 208, the size of an aperture of the optical assembly 202, and the time for which the image sensor 210 integrates charge. The amount of light provided to the image sensor 210 may be controlled by the camera control unit 300. For example, the camera control unit 300 includes an exposure controller 302, which responds to the amount of light available in the scene 110 given the intensity and spatial distribution of digitized signals corresponding to the intensity, and spatial distribution of the light focused on the image sensor 210. Exposure controller 302 may also control the aperture of the optical assembly 202 and, indirectly, the time for which the image sensor 210 integrates charge. The control connection from exposure controller 302 to the timing generator 212 is shown as a dotted line because the control is typically indirect.

Analog signals from the image sensor 210 are processed by analog signal processor 218 and applied to the A/D converter 220 for digitizing the analog signals from image sensor 210. The digitized signals, each representing streams of images or image representations based on the data, are transmitted to the image processor 304 as image signals 220.

The image processor 304 is disposed in the camera control unit 300 and is configured to perform digital image processing to process and filter, as appropriate, the received images. The image processor 304 may execute algorithms stored in a system memory 306 for processing the collected images. It should be noted that in some embodiments, the CCU, or some elements thereof, such as the image processor 304 may be contained with the camera head.

The CCU 300 further includes a system controller 308 configured to control the overall operation of medical imaging scope 200 based on a software program stored in system memory 306 and executed on a system processor. System memory 306 may store user settings and other data when the medical imaging scope 200 is turned off. In addition, the system controller 308 controls the sequence of data captured by directing the exposure controller 302 to set the light source 208 intensity and the size of the aperture of the optical assembly 202. Moreover, the system controller 308 may control various filters in optical assembly.

Processed image data is continuously sent to the video encoder 310 to produce a video signal that is processed by a display controller 312 and presented on image display 402. Image display 402 may be a liquid crystal display backlit with light-emitting diodes (LED LCD), although other displays known in the art may be used as well. The processed image data may be stored in system memory 306 or other internal or external memory devices, such as SD cards, USB drives, external hard drives, NVMe, or cloud-based storage solutions.

The user interface 400, including all or any combination of image display 402, user inputs 404, and status display 406, is controlled by a combination of one or more software programs executed by a system processor of the system controller 308, receiving input from user inputs 404. User inputs 404 may include but are not limited to signals received from keyboards, computer pointing devices, touch screens, voice command processing devices, or similar user input devices. It should be noted, of course, that some user input devices may be elements of the camera head 206. In addition, the system controller 308 manages the graphical user interface (GUI) presented on one or more image displays 402.

In addition to the system controller 308 and exposure controller 302, the electronic circuitry may include programmable logic devices, processors, and/or controllers. The image processor 304, system memory 306, video encoder 310, and display controller 312 may be housed within the CCU 300 or as part of a separate system. CCU 300 may be responsible for powering and controlling light source 208, the image sensor 210, and/or optical assembly 202, and may receive power and signals directly from the medical imaging scope 200 or indirectly by actuation of a user input 404, which may be, for example, on the image display 402, such as an icon on a touch screen, or by manipulation of a GUI via a mouse. Such power and control connections are not depicted separately but will typically be contained in a single flexible cable with data and power connections.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuits can be designated to perform all of the needed functions. All of these variations can perform the same function and fall within the scope of this invention.

With reference to again to FIG. 2 and now to FIGS. 3A and 3B, an illustrative depiction of a medical imaging scope 200 for use in an imaging system 100 is provided. The medical imaging scope 200 includes a camera head 204 coupled to an endoscope 206. The endoscope 206 may be fixedly or removably attached to the camera head 204 by any connection means 203 known in the art, such as with a bayonet connection, a screw connection, a friction fit, etc. Camera head 204 may include a first capacitive sensing unit 224 disposed along at least one surface 204a of the camera head 204, typically an outer surface. The first capacitive sensing unit 224 may include a plurality of capacitive sensors 224a and is configured to detect a touch by a user, including a grip of a user. In particular, the first capacitive sensing unit 224 may be provided as a sheet of material having electronic components, dielectric elements, or any other materials or components configured to sense a touch of the user. It should be appreciated that the term "outer surface" need not require that the capacitive sensors 224a are exposed to the environment but should be construed to mean that first capacitive sensing unit 224 and the plurality of capacitive sensors 224a are positioned adjacent to the outer surface to be able to receive tactile responses from a touch or grip of the user.

The camera head 204 includes an electronic controller 228 communicatively coupled to the first capacitive sensing unit 224 and can be configured to process the grip to determine a profile of the grip. The camera head 204 may further include a memory storage unit 230, although this memory storage unit may also be an element of the CCU 300. The memory storage unit 230 is a non-volatile, non-transitory memory configured to store an algorithm executable by the electronic controller 228 to perform one or more camera control functions. The memory storage unit 230 may further store an algorithm executable by the electronic controller 228 to process signals from the capacitive sensing unit 226 (which may comprise the first capacitive sensing unit 224 and second capacitive sensing unit 238) to determine the camera control function to be controlled and instructions for controlling the camera control function. The memory storage unit 230 may further store a plurality of grip profiles, each of the plurality of grip profiles being associated with a predetermined configuration of the one or more camera control functions.

The medical imaging scope 200 may be communicatively coupled with CCU 300. The system controller 308 of the CCU 300 receives signals from the electronic controller 228 to adjust the displayed image or control functions in accordance with the camera control function determined by the detected grip profile. For example, the first capacitive sensing unit 224 transmits signals to the electronic controller 228 as a result of the camera head 204 being gripped, wherein the electronic controller 228 processes the signals from the first capacitive sensing unit 224 to determine a profile of the detected grip. Based on the profile of the grip, the electronic controller 228 processes the memory storage unit 230 and configures the camera head 204 to operate in accordance with the predetermined configuration stored in the memory storage unit 230.

In another aspect, the electronic controller 228 may determine that there is no grip detected, and may, after a preset duration of time, perform operations to the imaging system 100. For example, the electronic controller 228 may indicate to the CCU 400, as a result of no grip being detected for, for example, 20 seconds, that the camera head has been put down, and thus the system should enter a stand-by mode, causing, for example, the light source 208 to be turned off or dimmed. Performing this operation can be most valuable, as the heat generated by an unattended endoscope can be a fire hazard. The required duration necessary to enter stand-by mode may be a function of the illumination intensity or may be preset by the user or manufacturer.

In another aspect, the electronic controller 228 may be configured to determine the handedness and/or identity of the user based on the profile of the grip. In response to determining the handedness of the user, the electronic controller 228 transmits the handedness of the user to the system controller 308, wherein the system controller 308 executes instructions stored on the system memory 306 to effectuate the camera control functions in a manner associated with the handedness. Various examples of such configuration are discussed below. Alternatively, the electronic controller 228 may be configured to process the detected handedness to operate the camera control functions associated with the detected handedness. Accordingly, it is appreciated by those skilled in the art that the electronic controller 228 and the system controller 308 may individually or collectively process the detected grip and/or handedness to operate the medical imaging scope 200 in accordance with the camera control functions associated with the detected grip.

As shown in FIGS. 3A and 3B, the first capacitive sensing unit 224 may be configured to substantially cover the entire outer surface 204a of the camera head 204. It should be appreciated that the arrangements of the first capacitive sensing unit 224, shown in FIGS. 3A and 3B, are illustrative and not limiting to the scope of the appended claims. The grip of the user is sensed by a predetermined group of first capacitive sensors 224a of the first capacitive sensing unit 224 to determine that the camera head 204 is being held by either a left or a right hand. As discussed above, the electronic controller 228 may further process the profile of the grip to determine the identity of the user and configure the medical imaging scope 200 with the preferences of the user (e.g., predetermined settings selected by the user) stored in the memory storage unit 230. In such an aspect, the electronic controller 228 may transmit the identity of the user to the system controller 308, wherein the system controller 308 executes instructions stored on the system memory 306 to effectuate the camera control functions in a manner associated with the user. Alternatively, the electronic controller 228 may be configured to process the identity of the user to operate the camera control functions associated with the determined identity. Additionally, the first capacitive sensors 224a may provide control means as well as identification means. For example, moving a forefinger along the underside of the camera head may operate a virtual "trigger" which may be programmed to control an element of the system, such as capturing a still image and storing it to memory, starting a recording of the captured image stream, switching between imaging modes, etc.

Camera head 204 may be defined as having a left side 232 and a right side 234, which is bifurcated along an axis running longitudinally along the length and center of camera head 204. As such, a determination of the handedness may be made, for example, simply based on the greater number of signals transmitted by the capacitive sensors 224a on the left side 232 of the camera head 204 relative to the right side 234 of the camera head 204. The electronic controller 228 may determine that a left hand is gripping the camera head 204 when the thumb and/or palm of the user are pressed along the left side 232 of the camera head 204. Likewise, the electronic controller 228 may determine that a right hand is gripping the camera head 204 (as shown by outline in FIG. 3) in instances where the number of signals from the first capacitive sensing unit 224 along the right side 234 of the camera head 204 is greater than the signals received from the left side 232 of the camera head 204. Of course, more complicated algorithms to determine handedness based on received signals from capacitive sensors 224a may also be employed. Once the handedness of the user is determined, the electronic controller 228 and/or the system controller 308 may further calibrate the medical imaging scope 200 to corresponding preferences based on the handedness. As an example, should the camera head 204 be held by the left hand of the user customizable control elements might be accordingly adjusted. For example, two programmable buttons (not shown) located on the camera head in a left and right position might be reassigned control capabilities that would correspond to the preferences of a left-handed user.

The electronic controller 228 is configured to process signals from the first capacitive sensing unit 224 and determine the identity of the user based on the signals from the capacitive sensors 224a. In such a process, distinctive biometric identifiers may be detected such as a palm print, a fingerprint, a grip profile, or the like. It should be noted that gloves are generally worn while operating in a surgical theater, therefore, while the intricacies of a fingerprint may not be detectable through a latex glove, for example, a grip profile may be detectable and a set of corresponding grip profiles may be stored in the memory storage unit 230, which may then be used to identify the user. However, it should also be noted that a fingerprint or similar identifying print may be used in a calibration stage prior to surgery (for example, upon receipt of the camera head from the vendor), after which the camera head may be disinfected prior to any use in a surgical procedure. Further not all medical interventions are conducted in a sterile environment, and therefore protective gloves are not always worn. In the first instance of use, the electronic controller 228 determines the identity of the user and associates the identity with a user profile stored in the memory storage unit 230 or system memory 306. For instance, the CCU 300 may be communicatively coupled to an image display 402 where the user inputs 404 (e.g., mouse, keyboard, and/or touch screen monitor, etc.) connected to the image display 402 may be used to enter a name and associate that user to the detected biometric identifier. The information may be stored in the memory storage unit 230 or system memory 306 so that the next time the user grips the camera head 204, the electronic controller 228 transmits the user identity to the system controller 308, and the system controller 308 actuates the CCU 300 to operate the imaging system 100 in accordance with the user preferences associated with the detected user identity. In an embodiment, a confirmation notification may be shown on the image display 402 to confirm that the identity of the user operating the imaging system 100 is correct.

Figure 4A:
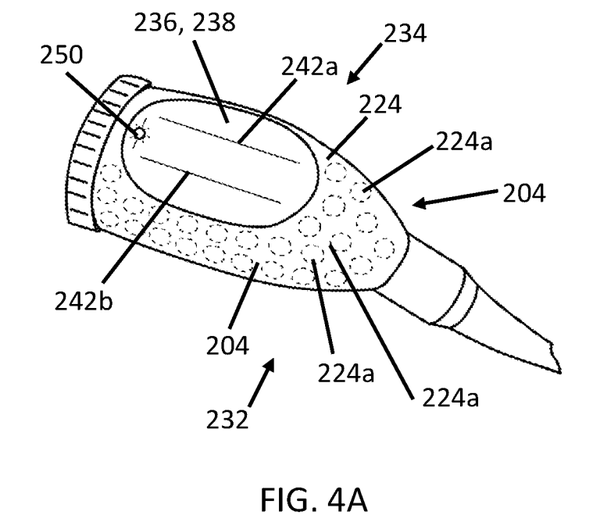
FIG. 4A is an illustrative depiction of a camera head held in the left hand of a user in accordance with the principles of an embodiment described herein.
Figure 4B:
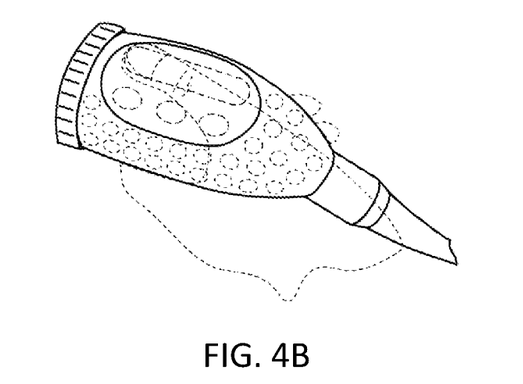
FIG. 4B is an illustrative depiction of a camera head held in the left hand of a user in accordance with the principles of an embodiment described herein.
Figure 4C:
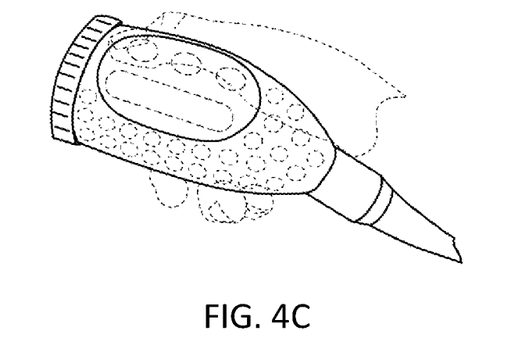
FIG. 4C is an illustrative depiction of a camera head held in the right hand of a user in accordance with the principles of an embodiment described herein.

As shown in FIGS. 4A, 4B, and 4C, the first capacitive sensing unit 224 includes a plurality of first capacitive sensors 224a configured to determine the handedness of the user by a predetermined pattern of a response received from the plurality of first capacitive sensors 224a. The first capacitive sensing unit 224 may also operate to control various camera and/or system functions as appropriate. Regarding the determination of handedness, as described above, the predetermined pattern may be stored in either the memory storage unit 230 or system memory 306, and user interface 400 may be used to associate the predetermined pattern with a user identity. As described above, the pattern may be based upon a left-handed and right-handed grip profile where signals from the first capacitive sensors 224a corresponding to the profile are processed to determine handedness. FIG. 4B shows, in broken lines, a likely grip profile for a left-handed person. FIG. 4C shows, in broken lines, a likely grip profile for a right handed person. In either case, the actuation of signals from each of the first capacitive sensors 224a within the broken lines is processed to determine handedness. It should be appreciated that there are many ways to determine the handedness other than a profile of a grip or a comparison of the actuation of first capacitive sensors 224a on one side versus the other (e.g., right side 234 vs. left side 232) and that the examples provided herein are not meant to limit the scope of the appended claims.

Referring to FIGS. 2-4C, camera head 204 of medical imaging scope 200 may include an input unit 236. The input unit 236 may be an element of the user input 404. In one aspect, the input unit 236 includes a second capacitive sensing unit 238; in another, the input unit 236 includes one or more buttons 240 in combination with the second capacitive sensing unit 238. The input unit 236 is disposed on camera head 204 and generally bound, or otherwise surrounded by the first capacitive sensing unit 224 to be readily identifiable and distinct. The input unit 236 is configured to allow the manual selection and control one of the plurality of camera control functions, such as zoom, focus, orientation, and/or brightness of the displayed image.

As shown in FIG. 3, various buttons 240 may be used in conjunction with a second capacitive sensing unit 238. Each of the buttons 240 may be depressible or otherwise actuatable and may be assigned, in some preferred embodiments, to designate the camera control function assigned to the second capacitive sensing unit 238, such as focus, zoom, brightness, image rotation, and the like. For instance, the first button 240a may be configured to designate the function of capacitive sensing unit 238 to control the zoom of the displayed image, the second button 240b may be configured to designate the function of capacitive sensing unit 238 to control the orientation of the image, and the third button 240c may be configured to designate the function of capacitive sensing unit 238 to control the focus of an image. The second capacitive sensing unit 238 incudes a plurality of second capacitive sensors, which may be arranged along axis and spaced apart from the buttons 240. The second capacitive sensing unit 238 is configured to control the camera control function designated by the selecting button 240. It should be appreciated that buttons 240 may be programmable, whereby the CCU 300 may display the plurality of camera control functions on the image display 402, and the user may select and assign a camera control function to a respective button 240. Medical imaging scope 200 is shown as having three (3) depressible buttons 240; however, it should be appreciated that medical imaging scope 200 may include one (1) or more buttons 240. In some embodiments, the electronic controller 228 is configured to process a sliding motion of the user's finger(s) or thumb along the second capacitive sensing unit 238 and convert the sliding motion into an input to control the selected camera control function. For instance, if a first button 240 is programmed to control the zoom of the image and is actuated, the user may slide their thumb or finger(s) along the second capacitive sensing unit 238 to increase or decrease the zoom of the displayed image. It should be appreciated that the electronic controller 228 may perform the selection and control individually or in combination with the system controller 308. Further a single button 240 may be used as a toggle, to toggle between various control functions assigned to the second capacitive sensing unit 238. For example, a first activation of button 240 could assign the function of the second capacitive sensing unit to control digital zoom, a subsequent activation of the button could assign the function of illumination intensity to the second capacitive sensing unit, a further subsequent activation of the button could assign the function of focus, etc. Further another example embodiment includes one where a first button 240 toggles between the various control functions assigned to the second capacitive sensing unit 238, and the remaining two buttons operate the same control function in a different manner. For example, the second capacitive sensing unit, operating as a slider, may allow the user to apply a digital zoom to the displayed image by moving a thumb up or down the slider. The second and third buttons 240, might provide the same control of zoom, but in a different manner, allowing more precise zoom control in a stepwise fashion, zooming in one unit by depressing the second button or zooming out one unit by depressing the third button. The user may then, for example, press the first button again to change the control of the second capacitive sensing unit (and the second and third buttons) to similarly control focus, and again to control image rotation, image brightness, etc.

It should also be noted that some embodiments include the second capacitive sensing unit but have no first capacitive sensing unit.

As shown in FIG. 4A, an embodiment of the input unit 236 is shown wherein no buttons 240 are presented, and wherein, for example, the controls 240 shown in FIG. 3 are replaced by capacitive touch controls, that are elements of, in some embodiments, a larger second capacitive sensing unit 238. In such an aspect, the selection of the camera control function is performed by an element of the second capacitive sensing unit 238. The second capacitive sensing unit 238 includes two rows 242a, 242b, of second capacitive sensors 238, each arranged along a common axis. In order to clearly delimit these two rows, in certain embodiments, the rows may be visually identified by printed lines, circles, symbols, etc. In such an aspect, row 242a may be assigned regions assigned to the selection of a control function, and row 242b may be configured to control the selected camera control function. In other words, the physical buttons shown in the embodiment shown in FIG. 3 are replaced with capacitive touch controls. Any number of "virtual buttons" may be present along this row 242a. For instance, an actuation or touch of a virtual button in row 242a may be processed by the electronic controller 228 to set a camera control function to be controlled by capacitive sensor along row 242b, this row now acting as the slider element 238 of FIG. 3. The selected camera control function may be transmitted from the electronic controller 228 to the system controller 308.

In this example, in order to facilitate the function currently being controlled by the virtual slider represented by second row 242b of the second capacitive sensing unit 238, an illuminating function indicator light 250 may be an element of the camera head 200. The function indicator light 250 may have associated therewith a specific color associated with each possible function control that may be assigned to the second row 242b of the second capacitive sensing unit 238. It should be noted that such a function indicator light may also be an element of the embodiment shown in FIG. 3 or embodiments described below. In such embodiments, the CCU 300 may be configured to indicate on the image display 402 which camera control function 248 is currently being controlled by the slider element, now present on row 242b, and may be displayed on the monitor in a color corresponding to the color of the function light 250 (See also FIGS. 6A-6C). This provides the user with two reference points confirming which camera control function 248 is being controlled by the second row 242b of the second capacitive sensing unit 238. Merely as an example: if the function indicator light 250 glows green, it indicates that zoom is being controlled by the slider; if the light glows blue, the slider is controlling the focus; if it glows red, it is controlling image rotation; if it glows white, it is controlling illumination intensity, etc.

With reference again to FIGS. 4B and 4C, the input unit 236 may be reconfigurable between at least a first configuration (shown in FIG. 4B) and a second configuration (shown in FIG. 4C). For example, the control and selection functions may be oriented in different positions depending on the user preference, or user handedness, as described below.

As an example of the versatility of the various embodiments, let us consider an embodiment where, as presented above, the second capacitive sensing unit 238, includes a first row 242a of second capacitive sensors 238 and a second row 242b of second capacitive sensors 238. Upon detecting the handedness of the user, the electronic controller 228 assigns to the first row 242a and the second row 242b a corresponding control function and a selection function that is more ergonomic for the handedness of the user. For instance, the electronic controller 228 may program the first row 242a of the second capacitive sensing unit 238 to perform a control function and the second row 242b to perform a selection function so as to form a first configuration (see FIG. 4B) or vice-versa so as to form a second configuration (see FIG. 4C) which is symmetrical to the first configuration. That is, if, for example as shown in FIG. 4B, the electronic controller 228 determines, by means of the first capacitive sensing unit 224, that the user is left-handed (or that the camera head 204 is being gripped by a left hand), the first row 242a is programmed to select a camera control function, i.e. that is operating as a row of virtual buttons, and the second row 242b is configured to perform a control of the selected camera control function, that is acting as a slider element. This provides a more ergonomic operation of the camera head 204 that might heretofore have been possible when a left handed person operates a camera head designed with a right-handed user in mind. Likewise, the assignment of properties of second capacitive sensors 238 along rows 242a and 242b may be reversed if the first capacitive sensing unit 224 determines that the camera head is being gripped by a right hand, as shown in FIG. 4C.

Likewise, the configuration of the second capacitive sensing unit 238 may be set based on the identity of the user detected by the first capacitive sensing unit 224. In such an aspect, the user may set up the imaging system 100 by confirming their identification with the detected biometric identifier, and the user may customize the configuration of the second capacitive sensing unit 238. For example, if the user is right-handed, imaging system 100 may be programmed to automatically configure the second row 242b to control a selected camera control function and the first row 242a to select the camera control function. However, the user may adjust this setting by actuating the user interface 400 to override this default setting and program the second row 242b to perform a camera selection function and the first row 242a to perform a slide function. In such a manner, a right-handed user may use their thumb to slide up and down along the first row 242a to control the selected camera control functions, in contrast to the configuration shown in FIG. 4C.

Figure 5A:
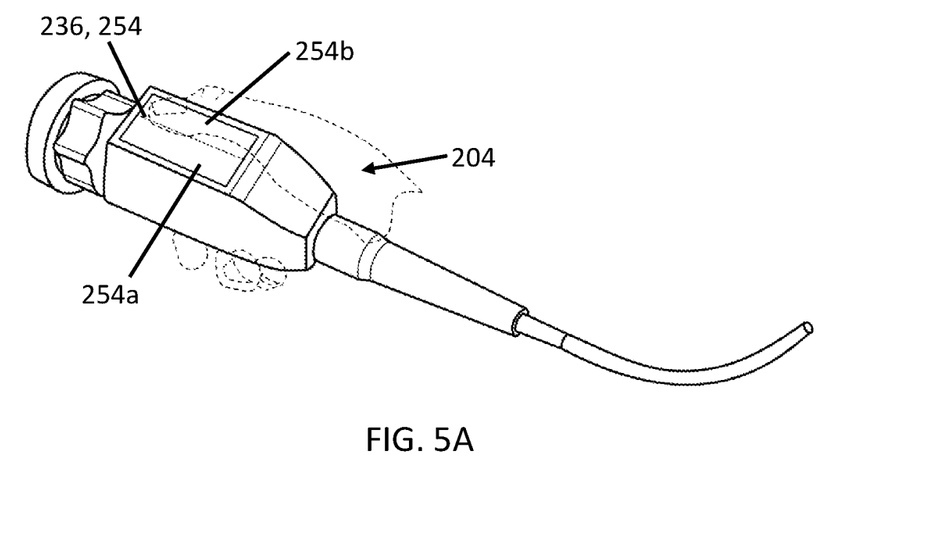
FIG. 5A is an illustrative depiction of the medical imaging scope held in the left hand of a user in accordance with the principles of an embodiment described herein.
Figure 5B:
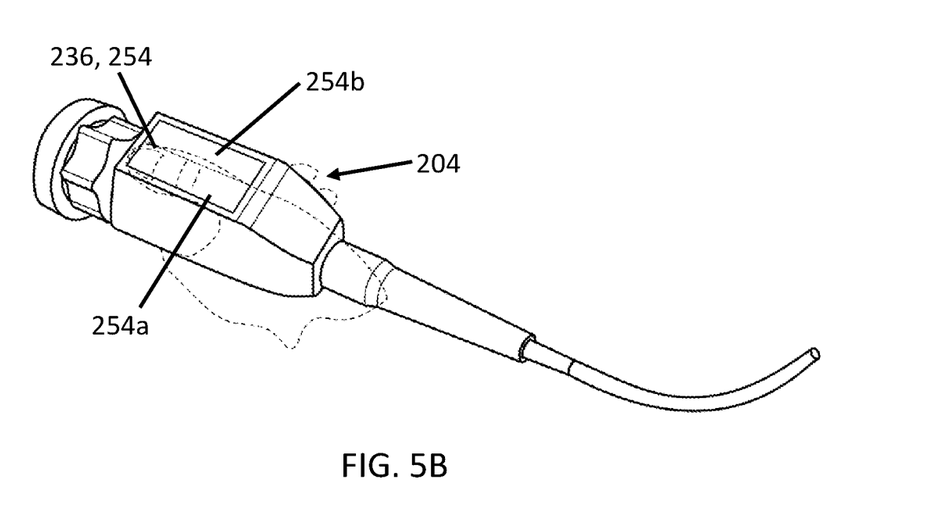
FIG. 5B is an illustrative depiction of the medical imaging scope held in the right hand of a user in accordance with the principles of an embodiment described herein.

In an embodiment of medical imaging scope 200 depicted in FIGS. 5A and 5B, the input unit 236 is a capacitive touch trackpad 254. Capacitive touch trackpads 254 are currently known, and any such capacitive touch trackpad 254 may be modified and adapted herein. Operation of the trackpad 254 may be based upon the handedness or identity of the user, in which case, for example, a left portion 254a of the trackpad 254 may be configured to select a camera control function, and the right portion 254b may be used to control the selected camera control function or vice versa based upon the handedness of the user. In other aspects, the configuration of trackpad 254 may be based on the identity of the user. For instance, by default, the electronic controller 228 may be configured to place the left portion 254a of the trackpad 254 to select a camera control function and the right portion 254b as a control function when the electronic controller 228 determines that the handedness is a left hand the left side of the trackpad 254. The imaging system 100 may be customized by the user to program, using the user interface 400, the trackpad 254 so as to configure the left portion 254a of the trackpad 254 as a control function and the right portion 254*b* to select a camera control function. In the aspect where the identity of the user is used to configure the trackpad 254, the user may customize the left portion 254*a* and the right portion 254*b* of the trackpad 254 for either a selection function or a control function, thus, changing the default of the electronic controller 228 based upon user preference.

Figure 6A:
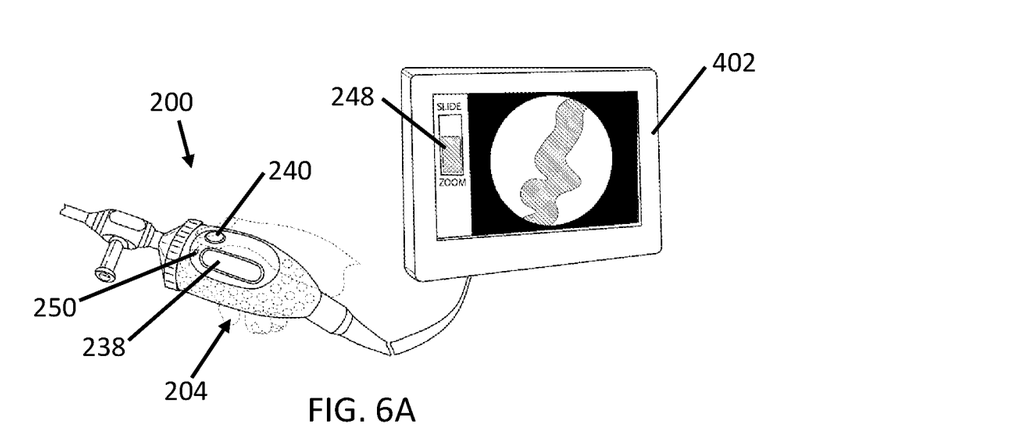
FIG. 6A is an illustrative depiction of a medical imaging scope depicting a zoom control function in accordance with the principles of an embodiment described herein.
Figure 6B:
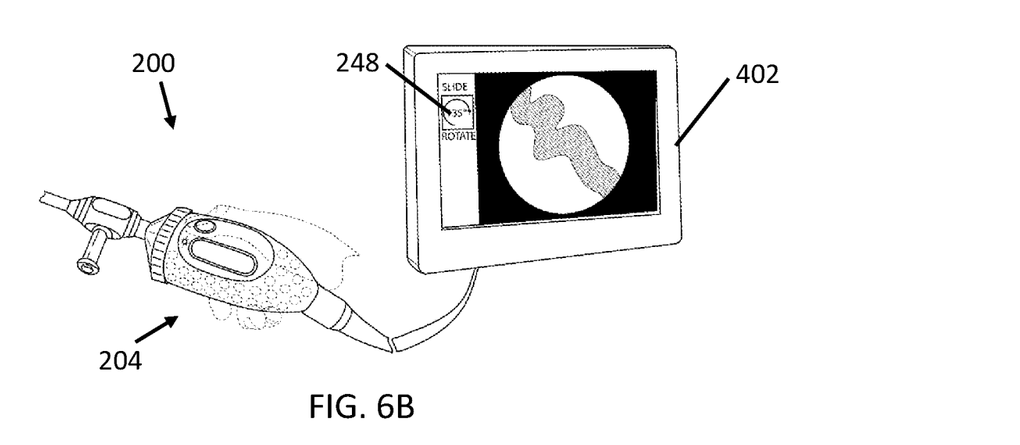
FIG. 6B is an illustrative depiction of a medical imaging scope depicting a camera display orientation control function in accordance with the principles of an embodiment described herein.
Figure 6C:
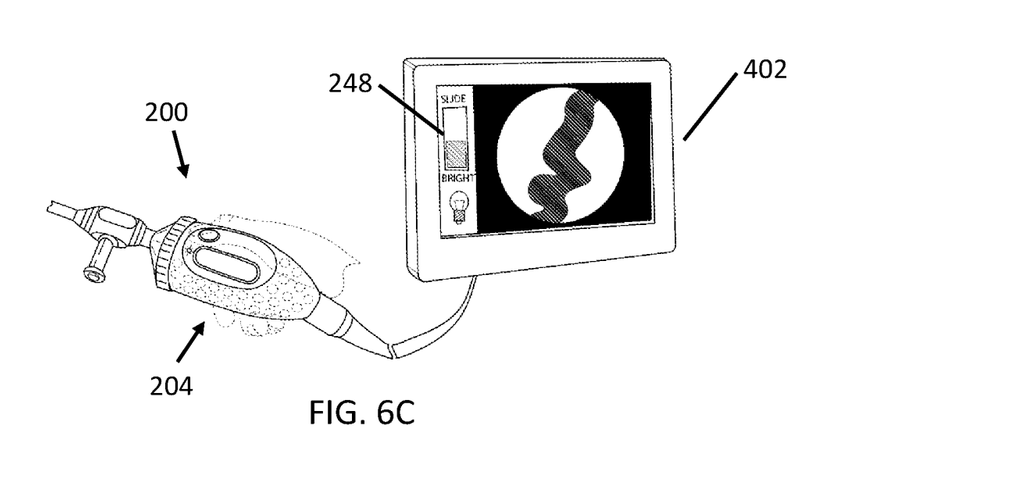
FIG. 6C is an illustrative depiction of a medical imaging scope depicting a brightness control function in accordance with the principles of an embodiment described herein.

With reference now to FIGS. 6A-6C, as an illustrative example of the operation of medical imaging scope 200 according to one possible embodiment described herein is shown. Though FIGS. 6A-6C depict an operation with respect to one embodiment, it should be appreciated that any of the embodiments (including combinations thereof) of the medical imaging scope 200 may be practiced herein and that the depiction of the other embodiments described herein are omitted purposefully as being redundant. With reference now to FIG. 6A, a first button 240 is pressed, wherein the second capacitive sensor 238, operating as a slider, is associated with a zoom function of the image, in which case the function light 250 glows in green on the camera head 204, and the image display 402 indicates that the zoom function is selected and has been assigned to the slider. The function light 250 is illuminated in a color that is the same as the color of the camera control function 248 displayed on image display 402, for this example, green, corresponding to the zoom function. Thus, the user is informed that it is a zoom controlled by the control feature of the second capacitive sensing unit 238. As the user slides their finger along the second row 242*b*, the degree of zoom is indicated on the image display 402.

FIG. 6B shows an aspect where the displayed rotation orientation is selected by pressing the button 240 a second time, and thus capacitive sensor 238 operating as a slider permits the image to be rotated by sliding a finger along the second capacitive sensing unit 238. The orientation is shown in a fixed position, and it should be appreciated that as the user slides their finger along second capacitive sensing unit 238, the image will rotate clockwise or counterclockwise. The direction in which the image is oriented is displayed as indicated by an arrow shown in a particular color as the camera control function 248 displayed on the monitor 402, for instance, red, corresponding to the color red which is illuminated by the function light 250 on the camera head 204.

FIG. 6C shows a depiction wherein the brightness of the image is selected by pressing the button 240 a third time, and again, the brightness may be increased or decreased by sliding a finger along the second capacitive sensing unit 238. The image brightness is indicated graphically as the camera control function 248 on a portion of the image display 402 in a color corresponding to a color illuminated by function light 250. For instance, the brightness function may be displayed as a metered bar in blue on the display, and the function light 250 may be configured to illuminate a blue light.

Figure 7:
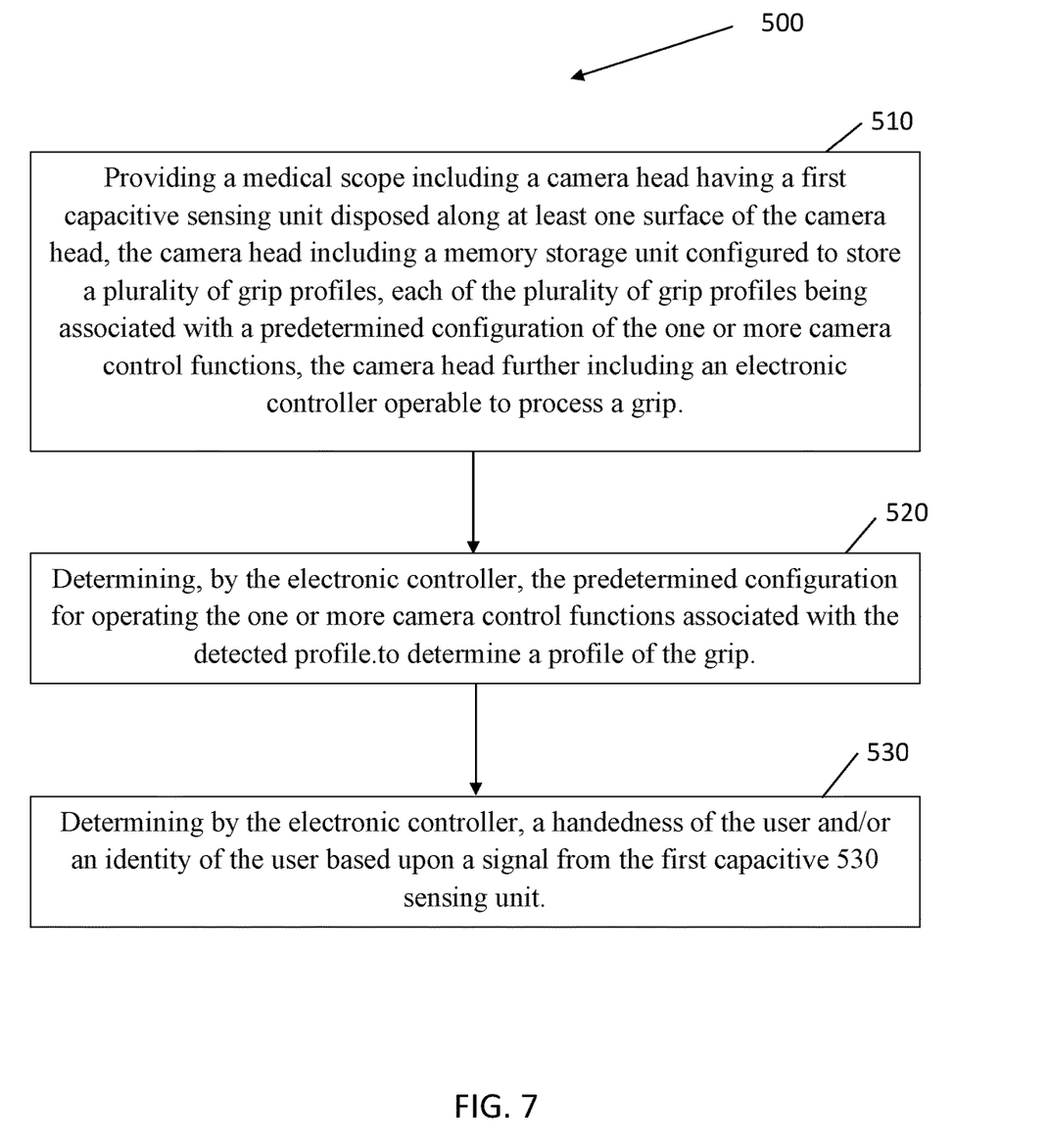
FIG. 7 is a flow chart showing the steps for a method of operating an imaging system.

With reference now to FIG. 7, a method 500 of operating an imaging system 100 is provided. At step 510, the method 500 includes the step of providing a medical imaging scope 200. The medical imaging scope 200 includes a camera head 204 having a first capacitive sensing unit 224 disposed along at least one surface 204*a* of the camera head 204, wherein the camera head 204 includes a memory storage unit 230 and an electronic controller 228. The memory storage unit is configured to store a plurality of grip profiles, each of the grip profiles is associated with a predetermined configuration of one or more camera control function. The electronic controller 228 is configured to process a grip to determine a profile of the grip. At step 520, the method 500 includes the step of determining, by the electronic controller 228, the predetermined configuration for operating the one or more camera control functions associated with the detected profile.

The method 500 may include the step 530 of determining by the electronic controller 228, a handedness of the user and/or an identity of the user based upon a signal from the first capacitive sensing unit 224. In an embodiment, the handedness of the user is determined by a predetermined pattern of a response from a plurality of capacitive sensors 224*a*. In such an embodiment, the electronic controller 228 may be further configured to process the determined handedness to actuate one or more of the camera control functions.

The identity of the user may be determined by the electronic controller 228 by processing the profile, processing a biometric identifier, such as a grip profile, a fingerprint, or a palm print detected by the first capacitive sensing unit 224. It should be appreciated that the identification of a user may also be determined by a predetermined pattern of a response from the first capacitive sensing unit 224 or by signing a signature on trackpad. In such an aspect, the electronic controller 228 may be further configured to actuate one or more camera control functions or pre-assigned control configurations associated with the determined user identification.

In yet another embodiment, the method 500 includes the step of providing an input unit 236 disposed on the camera head 204, the input unit 236 is configured to select and control one of a plurality of camera control functions. In such an embodiment, the input unit 236 may be a trackpad 254, a second capacitive sensing unit 238 having a plurality of second capacitive sensors, and/or a plurality of buttons 240 configured to select one of the camera control functions. The second capacitive sensing unit 238 is configured to detect a sliding motion and process the sliding motion by the electronic controller 228 to control a selected camera control function.

In yet another embodiment, the method 500 further includes the step of processing the detected handedness to generate a configuration for control. The configuration for control is an assignment of a predetermined arrangement of the second capacitive sensors 238 to generate a corresponding camera control functions configuration. In such an embodiment, the configuration for control includes a first configuration and a second configuration symmetrical to the first configuration. The configuration for control may include at least one capacitive sensor from the plurality of capacitive sensors programmed to select a camera control function from the plurality of camera control functions and at least two capacitive sensors from the plurality of capacitive sensors in a second capacitive sensing unit 238 programmed to control the selected camera control function by processing a sliding motion of the finger along the at least two capacitive sensors.

As used herein, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions, and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A camera head communicatively coupled to a camera control unit, the camera control unit configured to process data from the camera head to generate an image, the camera head comprising:
   a first capacitive sensing unit disposed along at least one surface of the camera head, the first capacitive sensing unit configured to detect a grip;
   an electronic controller communicatively coupled to the first capacitive sensing unit and operable to process the grip to determine a profile of the grip;
   a memory storage unit configured to store a plurality of grip profiles, each of the plurality of grip profiles being associated with a predetermined configuration of the one or more camera control functions; and
   wherein the electronic controller processes the profile of the grip to adjust the camera head to the predetermined configuration for operating the one or more camera control functions associated with the detected profile.

2. The camera head of claim 1, wherein the profile is processed to determine a handedness of the user.

3. The camera head of claim 1, wherein the electronic controller processes the profile of the grip to determine an identification of a user and adjust the camera head to the predetermined configuration associated with the identified user.

4. The camera head of claim 1, wherein the electronic controller is configured to adjust the intensity of a light source when the grip is not detected for a first duration.

5. The camera head of claim 1, wherein the camera head further includes an input disposed on the at least one surface of the camera head, the input configured to select and control the one or more camera control functions.

6. The camera head of claim 5, wherein the one or more camera control functions includes a zoom, a focus, an image orientation, a brightness of an image, and an illumination intensity.

7. The camera head of claim 5, wherein the input is a trackpad.

8. The camera head of claim 1, wherein the input includes a second capacitive sensing unit having a plurality of second capacitive sensors, the second capacitive sensing unit bound by the first capacitive sensing unit.

9. The camera head of claim 8, wherein the input further includes a plurality of buttons, each of the plurality of buttons configured to select one of the plurality of camera control functions, wherein the second capacitive sensing unit is configured to control the selected one of the plurality of camera functions.

10. The camera head of claim 8, wherein the second capacitive sensing unit is configured to detect a sliding motion.

11. The camera head of claim 10, wherein the second capacitive sensing unit includes a plurality of second capacitive sensors, and wherein the electronic controller is programmed to process the profile to determine a handedness and generate a configuration for control, the configuration for control being an arrangement of second capacitive sensors of the plurality of second capacitive sensors to generate a corresponding one of the plurality of camera control functions.

12. The camera head of claim 11, wherein the configuration for control includes a first configuration and a second configuration symmetrical to the first configuration.

13. A camera head communicatively coupled to a camera control unit, the camera control unit configured to process data from the camera head to generate an image, the camera head comprising:
   a first capacitive sensing unit disposed along at least one surface of the camera head; and
   an input disposed on the camera head, the input configured to select and control one or more camera control functions;
   wherein the input includes a second capacitive sensing unit having a plurality of second capacitive sensors, the second capacitive sensing unit bound by the first capacitive sensing unit.

14. The endoscopic imaging system of claim 13, wherein the one or more camera control functions includes a zoom, a focus, an orientation, and a brightness of an image.

15. The endoscopic imaging system of claim 13, wherein the input is a trackpad.

* * * * *